(12) United States Patent
Alleyne

(10) Patent No.: US 6,454,767 B2
(45) Date of Patent: Sep. 24, 2002

(54) PROTECTION DEVICE

(76) Inventor: Neville Alleyne, 9687 Claiborne Square, La Jolla, CA (US) 92037

( * ) Notice: Subject to any disclaimer, the term of this patent is extended or adjusted under 35 U.S.C. 154(b) by 0 days.

(21) Appl. No.: 09/246,274

(22) Filed: Feb. 8, 1999

Related U.S. Application Data (63) Continuation of application No. 08/769,508, filed on Dec. 19, 1996, now Pat. No. 5,868,745, which is a continuation of application No. 08/440,363, filed on May 12, 1995, now Pat. No. 5,611,354, which is a continuation of application No. 08/152,433, filed on Nov. 12, 1993, now abandoned, which is a continuation-in-part of application No. 07/975,106, filed on Nov. 12, 1992, now abandoned.

(51) Int. Cl.⁷ .............................................. A61B 17/56
(52) U.S. Cl. .......................................... 606/61; 128/888
(58) Field of Search ................. 128/846, 888, 128/889; 606/60, 61

(56) References Cited

U.S. PATENT DOCUMENTS

| | | | | |
|---|---|---|---|---|
| 2,443,481 A | * | 6/1948 | Sene | 128/888 |
| 3,044,497 A | | 7/1962 | Rebut | |
| 3,108,399 A | | 4/1963 | Eitenmuller | |
| 3,256,877 A | | 6/1966 | Haboush | |
| 3,693,616 A | | 9/1972 | Roaf | |
| 3,993,078 A | | 11/1976 | Bergentz et al. | |
| 4,013,078 A | | 3/1977 | Feild | |
| 4,023,569 A | * | 5/1977 | Warnecke | 128/888 |
| 4,134,399 A | * | 1/1979 | Halderson | 128/888 |
| 4,164,794 A | | 8/1979 | Spector | |
| 4,401,112 A | | 8/1983 | Rezaian | |
| 4,583,541 A | | 4/1986 | Barry | |
| 4,599,085 A | | 7/1986 | Riess | |
| 4,599,086 A | | 7/1986 | Doty | |
| 4,603,695 A | * | 8/1986 | Ikada et al. | |
| 4,705,031 A | | 11/1987 | Wolter | |
| 4,773,402 A | | 9/1988 | Asher | |
| 4,794,918 A | * | 1/1989 | Wolter | 128/920 P |
| 4,892,545 A | | 1/1990 | Day et al. | |
| 4,973,332 A | | 11/1990 | Kummer | |
| 5,000,166 A | | 3/1991 | Karpf | |
| 5,041,113 A | | 8/1991 | Biedermara | |
| 5,052,373 A | | 10/1991 | Michelson | |
| 5,108,395 A | | 4/1992 | Laurain | |
| 5,113,685 A | | 5/1992 | Asher | |
| 5,139,498 A | | 8/1992 | Astudillo | |
| 5,190,759 A | | 3/1993 | Lindlad et al. | |
| 5,242,443 A | | 9/1993 | Kambin | |
| 5,261,908 A | | 11/1993 | Campbell | |
| 5,366,455 A | | 11/1994 | Dove | |

FOREIGN PATENT DOCUMENTS

| | | |
|---|---|---|
| FR | 052880 | 8/1945 |
| FR | 1004625 | 4/1952 |
| FR | 2386301 | 11/1978 |

OTHER PUBLICATIONS

LaRocca, et al. J. Boone Joint Surg. 56: 545–550 (1974).
Barbera, et al. J. Neurosurg 49: 419–424 (1978).
Boot, et al. Clin. Orthopedics & Related Res. 215: 296–302 (1987).
Cooper, et al. Spine 16(9): 1044–1048 (1991).
Gill, et al. Spine 6 (2) : 191–192 (1981). Gill, et al. Spine 4 (2) : 176–186 (1979).
Jacobs, et al. Spine 5 (3) : 223–29 (1980).
Keller, et al. J. Neurosurg. 49: 412–418 (1978).
Kiviluoto, O. "Use of Free Fat Transplants to Prevent Epidural Scar Formation" *Acta Orthopaedica Scandinavica* 164: Chapters 1–6 (1976).

(List continued on next page.)

*Primary Examiner*—Michael A. Brown
(74) *Attorney, Agent, or Firm*—Knobbe Martens Olson & Bear LLP (57) ABSTRACT

A spinal protection device is provided which minimizes the formation of post-operative adhesions. The protection device may comprise a fenestrated shield, and may be positioned such that contact between the shield and the spinal dura is substantially avoided.

6 Claims, 6 Drawing Sheets

OTHER PUBLICATIONS

Kuivila, et al. Clin. Orthpedics & Related Res. 236: 166–174 (1988).
Lawson, et al. Spine 16 (6) : S222–S226 (1991).
Lee, et al. Spine 9(3) : 305–312 (1984).*
Mayfield, F. "Autologous Fat Transplants for the protection and Repair of the Spinal Dura" Clin. Neurosurgery Chapter 19: 349–361.*

Mikawa, et al. Spine 11(8) : 843–846 (1986).*
Nussbaum, et al. Neurosurgery 26 (4) : 649–654 (1990).*
Songer, et al. Spine 15 (6) : 550–554 (1990).*
Verardi, G. Chir. Organi. Mov. 65: 147–151 (1990).*
Wujek, et al. Exp. Neurology 114: 237–245 (1991).*

* cited by examiner

PROTECTION DEVICE

CROSS REFERENCE TO RELATED APPLICATIONS

This application claims priority to is a continuation of U.S. patent application Ser. No. 08/769,508, now U.S. Pat. No. 5,868,745, filed Dec. 19, 1996, which is a continuation of U.S. patent application Ser. No. 08/440,363, filed May 12, 1995, now U.S. Pat. No. 5,611,354, which is a continuation of U.S. patent application Ser. No. 08/152,433, filed Nov. 12, 1993, abandoned, which is a continuation-in-part of U.S. patent application Ser. No. 07/975,106 filed Nov. 12, 1992, now abandoned. The disclosures of U.S. Pat. Nos. 5,868,745, 5,611,354, and 5,437,672 are hereby incorporated by reference in their entireties.

BACKGROUND OF THE INVENTION

Adhesions commonly form between an organ and surrounding connective tissue and bone after a surgical procedure. Following surgical trauma, connective tissue surrounding the organ proliferates to from a fibrous mass that binds the organ to neighboring organs, viscera, muscle, or bone. Depending on the type of surgery and the location of the incision, the adhesions may produce negligible discomfort or severe pain. However, adhesion formation can significantly complicate subsequent surgical procedures at the same or adjacent sites. Repeat surgical procedures are fairly frequent in the back, cardiac, abdomen and cranium. The presence of post-operative adhesions from a prior surgery complicates the second surgery because the contacts between the target organ and the neighboring bone and connective tissue must be carefully dissected away before the surgeon can initiate the corrective surgical procedure. The surgeon risks damaging the target organ during the dissection and the time required for the dissection procedures adds to the total time that the patient is under general anesthesia.

An unfortunate consequence of modern back surgery, whether lumbar, thoracic, or cervical surgery, is the formation of post-operative scar tissue. Scar formation surrounding the dura and nerve roots oftentimes will compress the nerve roots and cauda equina, thereby producing neural complications such as persistent low back pain, sciatica, and/or bowel and bladder dysfunction. Multiple revision operations may prove necessary due to recurrent disk herniation, post-operative spinal stenosis (iatrogenic or acquired), or because of exuberant epidural fibrosis.

Scar tissue formation after laminectomies and laminotomies for disk excision or a decompressive laminectomy for spinal stenosis present both surgeon and patient with an additional post-operative concern. Laminectomies and laminotomies frequently remove bone tissue and leave the dura exposed. Post laminectomy scar tissue, also termed epidural fibrosis, is primarily formed from fibrous connective tissue and develops in the post-operative hematoma that forms between the paraspinous muscles and the dura. The dura is relatively thin and can easily be injured during surgery. In particular, the dura is susceptible to damage during revision surgery when scar tissue adheres to the dura making it difficult for the surgeon to perform an adequate neurolysis. Thus, a method is needed for protecting the dura from scar tissue adhesion.

At the present time, methods to minimize the amount of scar tissue include the use of autogenous fat grafts, gelatin foams or sponges, or microfibullary collagen as an interposing protective layer between the spinal dura and the adjacent viscera. Other biological substances and chemical compounds that have been tested experimentally for their usefulness in animals include bone grafts, microfibrillar collagen, elastase, polyethylene, mylar, dacron, teflon and methylmethacrylate.

Autogenous fat grafts have been used following laminectomies as early as 1964. The fat is placed over the exposed dura after removal of the lamina or a portion of the lamina. The fat provides a protective barrier for the dura, and may limit scar formation between the muscle and the dural tissue. However, fat grafts are known to frequently adhere to the dura. These adhesions complicate revision surgery because they require tedious dissection by the orthopaedic or neurosurgeon. Fat grafts are preferably harvested from a sight close to the surgical incision, such as the subdermal areolar tissue bed. However, unless the patients are overweight, fat harvesting from nearby locations is not always possible, particularly in multiple laminectomy procedures. Further, fat harvesting may require a second incision. The incisions at the secondary locations may sometimes lead to complications such as hematoma formation or dimpling in the skin.

Other substances are used where fat grafts are not possible or desired. Gelatin foam (such as Gelfoam® sponge, supplied by Upjohn Company Inc., Kalamazoo, Mich.), or polylactic acid (PLA) is a useful substitute for autogenous fat grafts. This material is also placed over the dura to reduce scar formation. There is some controversy concerning the preference of gelatin foams or sponges versus fat; however, neither is optimal. Like fat, gelatin foams or sponges may move out of position following surgery. Furthermore, while fat and gelatin foams may form a barrier between the visceral tissue and the dura, there is a propensity for both fat and gelatin foam or sponge to adhere to the dura. Neither fat nor gelatin foam provides adequate physical protection to the cauda equina.

A mechanical barrier that would provide support to the spinal dura as well as reduce scar formation is needed. U.S. Pat. No. 4,013,078 to Feild discloses a device for preventing adhesions between the patient's dura and spinal nerves and other anatomic structures following spinal surgery. The device includes a conduit sheath of teflon or silicone that is positioned in close proximity to the nerve root. Like the previous protective overlay substances, such a device is invasive to the neuroforamen and anchors directly to the dura. This in turn would promote adhesions between the dura and the protecting device creating unnecessary complications for revision surgery.

In order to minimize the surgical time for dissection, minimize nerve injury and minimize dural tears a spinal cord protection device should be simple to insert, non-invasive to the dura and maintain a distance from the neural tissues. Preferably, anchoring means should contact bone instead of tissue prone to scar formation to minimize post-operative epidural fibrosis. Finally, the optimal mechanical device is readily contoured to provide a customized mechanical barrier to prevent dural or nerve root injury. Preferably, the device is adaptable in design to accommodate other surgical devices used in back surgery. Such a device is provided in the detailed description of this invention.

Adhesions also form between the heart and the anterior thoracic skeleton following cardiac surgery. In particular, adhesions form between the posterior surface of the sternum and the anterior surfaces of the heart. Repeat open heart surgeries are complicated by adhesion formation because the scar tissue must be dissected away before the sternum can be cut lengthwise and before the anterior thoracic skeleton can be retracted to expose the heart. For example, it is estimated that there are at least 250,000 coronary artery bypass graft surgeries done each year in the United States. Approximately 20% of these surgeries are revision surgeries. Adhesions form between the greater vessels of the heart and the posterior surface of the sternum. The adhesions make the separation of the pericardium from the sternum difficult and thus create severe complications during revision surgeries. It is estimated that 2 to 4% of the revision surgeries end in fatality as a result of adhesion-induced complications. Therefore, there is a need for a device that minimizes adhesion formation. The present device fulfills this need. Moreover, the device is simple to insert, easy to remove and prevents the formation of adhesions between the heart and the posterior surface of the sternum.

SUMMARY OF THE INVENTION

The present invention comprises methods and apparatus for spinal protection following spinal surgeries. In one embodiment, the invention comprises a biocompatible protection device comprising a shield adapted to cover a bony dissection in the spine of a vertebra. The shield may include attachment ports and fenestrations.

DETAILED DESCRIPTION OF THE PREFERRED EMBODIMENT

Back surgery including laminectomies, hemilaminectomies spinal stenosis surgery, and diskectomies, including microdiskectomies, involve the removal of vertebral bone tissue to gain access to the spinal foramen. This bone removal leaves the spinal dura exposed and unprotected. Following surgery, scar tissue frequently forms between the dura and the surrounding tissue. Research indicates that the epidural scar is principally formed from fibroblasts derived from the damaged erector spinae muscles that overlay the laminectomy site (LaRocca, et al. *J. Bone Joint Surg.* 56B:545–550, 1974). These cells form adhesions that bind the muscle tissue to the fragile dura. As a result of adhesion formation, spinal mobility is reduced and the adhesions often lead to pain and slow post-operative recovery. The device of this invention advantageously operates to prevent adhesion formation and to physically protect the dura, now exposed by surgery. In addition, the device of this invention facilitates future revision surgery.

While this invention will be discussed as it relates to spinal surgery, it is contemplated within the scope of this invention that the shield of this invention is suitable as a protective covering for any bony dissection in a vertebrate. Therefore, while a preferred embodiment of this invention relates to the use of the shield to cover a bony dissection of a vertebrae, the shield device could similarly be used to cover a bony dissection associated with open heart surgery, the bony dissection of the cranium, or the like. Those with skill in the art of orthopaedics or neurosurgery will be able to generate formed shields, anchorable to bone, that will accommodate bony dissections in a variety of skeletal tissues.

Figure 1:
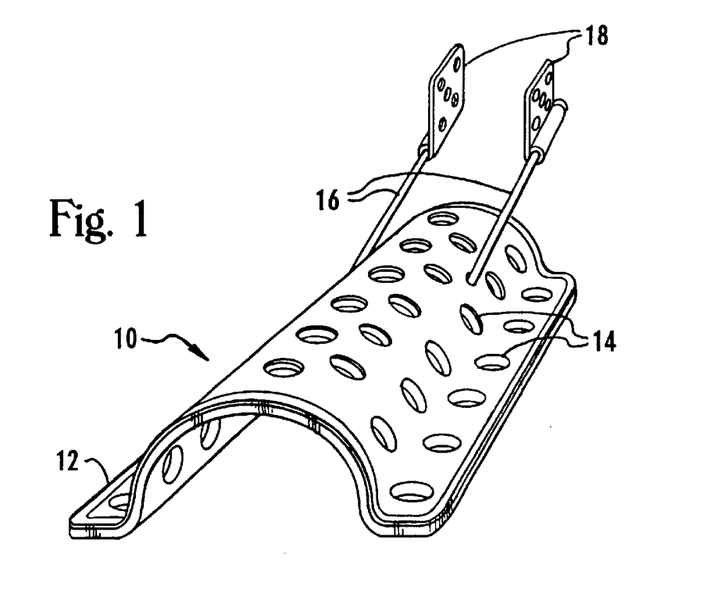
FIG. 1 is a right-front perspective view of the preferred embodiment, showing the arched shield and attachment arms.
Figure 3A:
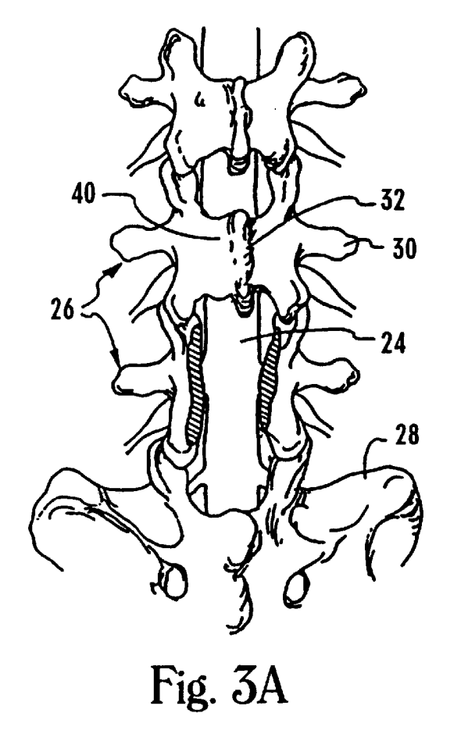
FIG. 3A is a partial perspective view of lumbar vertebrae illustrating the bony dissection associated with a laminectomy.

FIG. 1 provides an exemplary drawing of a preferred embodiment of this invention. The invention provides a formed shield 10 adapted to fit onto at least one vertebral facet (not shown in FIG. 3) to cover the bony dissection associated with a hemilaminectomy procedure, a laminectomy procedure or the like. As diagrammed in FIG. 1, a main body 11 of the shield 10 is molded or formed preferably as an arch or semi-cylinder. The arch flattens out on each side of the main body 11, forming a pair of support planes 12. The support planes 12 provide a surface area suitable for resting the shield 10 against the vertebral bone. The arched contours of the main body 11 prevent contact of the main body 11 with the spinal dura or nerve roots, thereby minimizing further trauma to the spinal dura and preventing the formation of adhesions and scar tissue between the underside of the device and the spinal dura.

As will be discussed in the context of FIGS. 4 and 5, the removal of vertebral bone along the spinal column leaves the cauda equina susceptible to physical trauma. Products such as gelatin foam or fat do not provide a sufficient barrier to prevent potential physical trauma. The shield 10 of the present invention advantageously rests on bone to minimize the contact between the device and the spinal dura and surrounding neural tissues. Such reduced contact minimizes adhesion formation between the neural tissues and the device itself.

In a preferred embodiment of this invention, a plurality of fenestrations 14 are formed in the surface of the shield 10. It is contemplated within the scope of this invention that the fenestrations 14 may take any number of forms or shapes, and those depicted in the figures are to be viewed as exemplary. The fenestrations 14 are distributed across the surface of the shield 10 and are designed to prevent the retention of fluid within the vertebral canal. Absent such openings, liquids such as cerebral spinal fluid, blood, and irrigation fluid associated with surgery could potentially accumulate beneath the shield 10 and create harmful pressure on the cauda equina and associated neural tissue. Following surgery the fenestrations 14 serve as out-flow ports to relieve pressure associated with the accumulation of fluid beneath the device during the healing process. Optionally, the fenestrations 14 may be covered with a filter, mesh, or the like (not shown), to prevent the extension of scar tissue formation into the fenestrations 14 while permitting the passage of fluid through the shield 10.

In another preferred embodiment of this invention, the device is associated with a surgical drain (not shown) to further facilitate fluid egress from the surgical site. Such surgical drains are well known in the art and it is contemplated that the device of this invention is adapted to accommodate a drain or in another embodiment a drain is directly incorporated into the device.

When positioned correctly over the bony dissection, it is unlikely that the shield 10 would move. Thus, although not necessary to the function of the present invention, it is understood that most surgeons would likely prefer to anchor the shield 10 in place following surgery.

The attachment means contemplated for use with the shield 10 of the present invention can take any number of forms. In a preferred embodiment, the attachment is to bone. Bone attachment contemplated within the scope of this invention include, but are not limited to, both attachment to adjacent spinous processes and lateral attachments such as to facets, transverse processes, articulating processes or the like. It is desirable that no contact is made with the neural elements. Preferably, the attachment means does not extend into the spinal canal or neuroforamen to an extent that would make contact with the dura or nerve roots likely.

Figure 2:
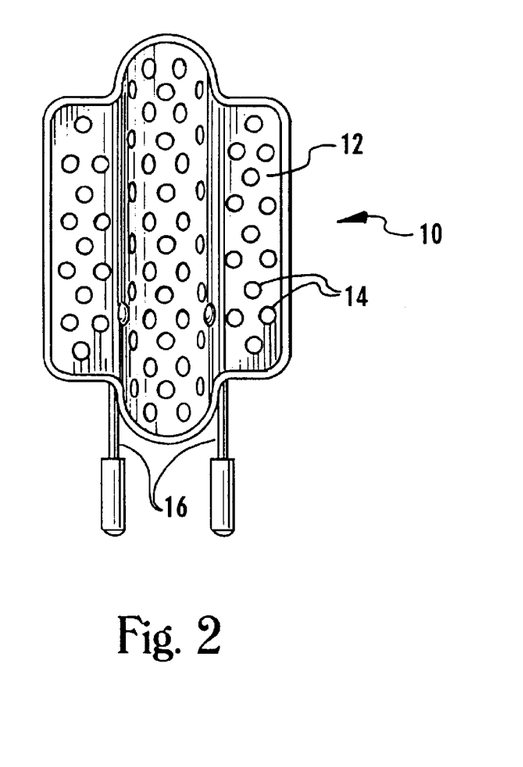
FIG. 2 is a bottom plan view showing the arched shield and attachment arms of FIG. 1.

In a preferred embodiment, the attachment means is a pair of attachment arms 16 attached to the main body 11 of the shield 10. Preferably, each of the attachment arms 16 comprise a rod 17 that is attached to and extends, at an acute angle, from the main body 11 of the shield 10. In this embodiment, the rods 17 are used to attach the shield 10 to an inferior or superior spinous process (see FIGS. 4A and 4B). The actual attachment to the spinous process may take any form known in the art. In a preferred embodiment the rods 17 terminate in a pair of attachment flags 18. As shown in FIG. 1, the flags 18 are provided with a plurality of pin holes 19 to facilitate their attachment to an adjacent spinous process. In another embodiment, the attachment means is through the use of surgical wire, staples or the like. The pins, wire or other attachment means contemplated within this invention, whether in the form of the rods 17 or otherwise, are prepared from surgical steel, tungsten, titanium or other suitable materials. FIG. 2 clearly illustrates the manner in which the attachment means laterally extend beyond the "footprint" of the main body 11.

Advantageously, the fenestrations 14 may also serve as attachment means. For example, suture or wire is useful for attaching the shield 10 to bone by being passed through the fenestrations 14, binding the shield 10 to adjacent bone. Similarly, it is contemplated that in such cases where necessary, the shield 10 is stabilized to cartilage ligament or adjacent muscle tissue. In either case, the fenestrations 14 ably serve as anchoring points over the entire surface of the shield 10, as required.

The actual dimensions of the shield 10 will vary depending on the particular surgical procedure. In a preferred embodiment, the device is prepared in a size and shape to accommodate a laminectomy. Laminectomies are used for spinal stenosis surgery, for central disk herniation, for an osteophyte centrally, for intradural tumors or for other conditions such as epidural abscesses. Laminectomies result in the exposure of the right and left nerve root axilla and the central cauda. The application of the device to a bony dissection following a laminectomy procedure is illustrated in FIGS. 3A, 3B and 3C.

FIG. 3A is an illustration of a laminectomy of the fifth lumbar vertebrae. A spinal cord 24 is schematically depicted, surrounded by a vertebral column composed of individual lumbar vertebrae 26, and the sacrum 28. Although the shape of the individual vertebrae 28 does vary, each are composed of a transverse process 30 and a spinous process 32.

Figure 3B:
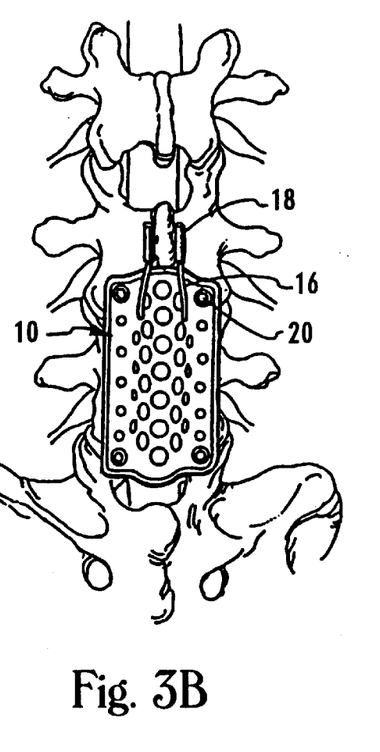
FIG. 3B is a partial perspective view, similar to FIG. 3A, showing use of the shield device to cover the laminectomy defect in accordance with the present invention.

A preferred application of the shield 10 is provided in FIG. 3B. The shield 10 is positioned over the laminectomy site and the attachment arms 16, terminating here, in attachment flags 18, are used to attach the device to the spinous process 32 of the fourth lumbar vertebrae 26. In addition to the attachment arms 16, in this embodiment, a set of four attachment pins 20 are used to anchor the four corners of the shield 10 in place to the surrounding vertebrae tissue.

Figure 3C:
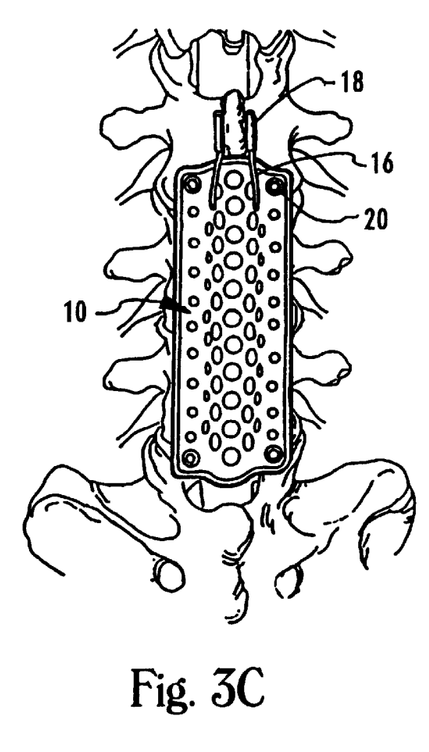
FIG. 3C is a partial perspective view showing the use of an elongated shield device to cover a laminectomy defect associated with two vertebrae.

FIG. 3C illustrates another preferred embodiment of the invention. In FIG. 3C, the shield 10 is designed to span a laminectomy defect involving two vertebrae. Attachment arms 16 and attachment flags 18 are similarly positioned on the shield 10 of FIG. 3C. In this embodiment, the shield 10 is adapted to span at least two vertebrae. It is contemplated that the shield 10 is prepared in a length and width to accommodate laminectomies involving three or more vertebrae.

In the embodiment illustrated in FIGS. 3A and 3B, it is contemplated that the overall length of the shield 10 will be at least as long as a lateral length 1 of the lamina surface of the vertebrae 26 containing the laminotomy defect, and wide enough to stably mate with the remaining lateral lamina surfaces of bone following the laminectomy procedure. Therefore, it is contemplated that the overall length of the shield 10 for use in spanning one laminectomy defect (or hemilaminectomy defect, see FIGS. 4A and 4B) ranges in size from about 2.0 cm to 6.0 cm and preferably between 2.5 cm to 4.5 cm, with a final width ranging from about 1.5 cm to 4.5 cm, and preferably between about 2.0 cm to 3.5 cm.

Customization of the final size and shape of the shield 10 by the surgeon will produce a size suitable for each individual patient. The optimal thickness of the shield 10 will vary depending on the plasticity or moldability of the device, which in turn will depend on the choice of shield material. However, it is contemplated that a preferred thickness of the shield 10 should be approximately 0.5 mm to 8 mm and more preferably, about 0.5 mm to 5 mm.

Figure 4A:
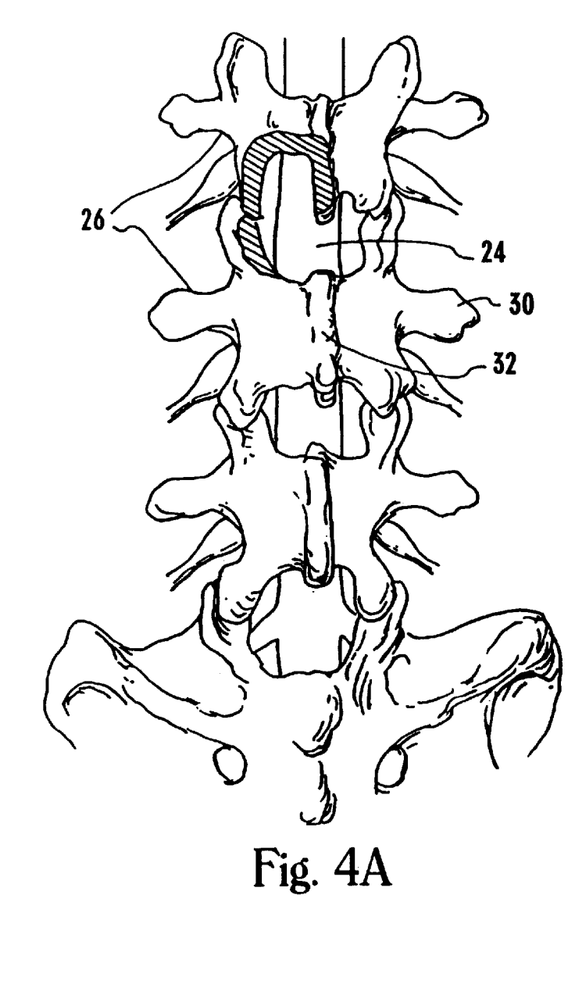
FIG. 4A is a partial perspective view of lumbar vertebrae illustrating the bony dissection associated with a hemilaminectomy.
Figure 4B:
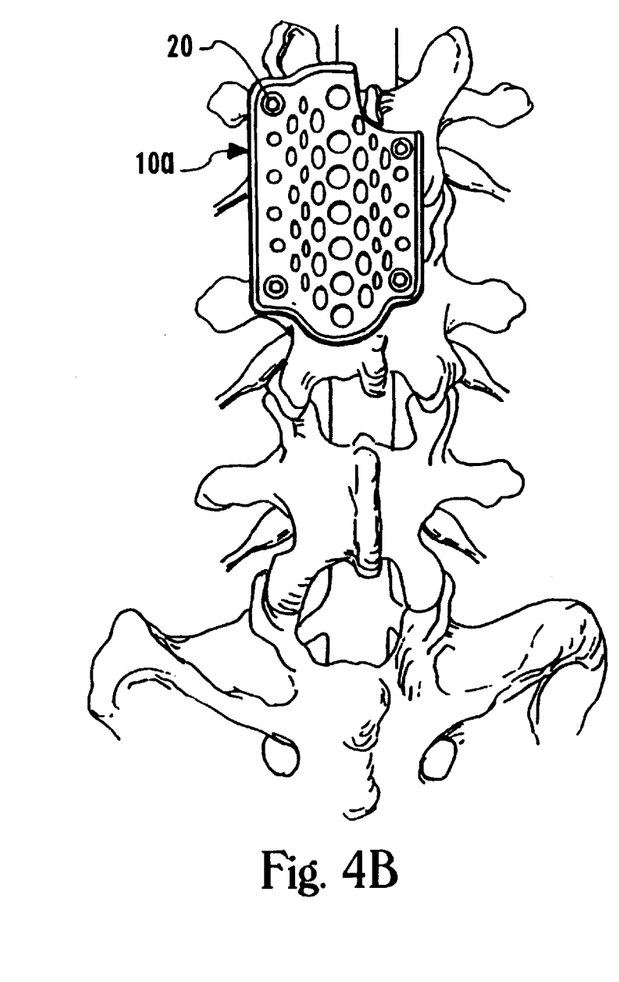
FIG. 4B is a partial perspective view, similar to FIG. 4A, showing use of the shield device to cover the hemilaminectomy defect in accordance with the present invention.
Figure 5:
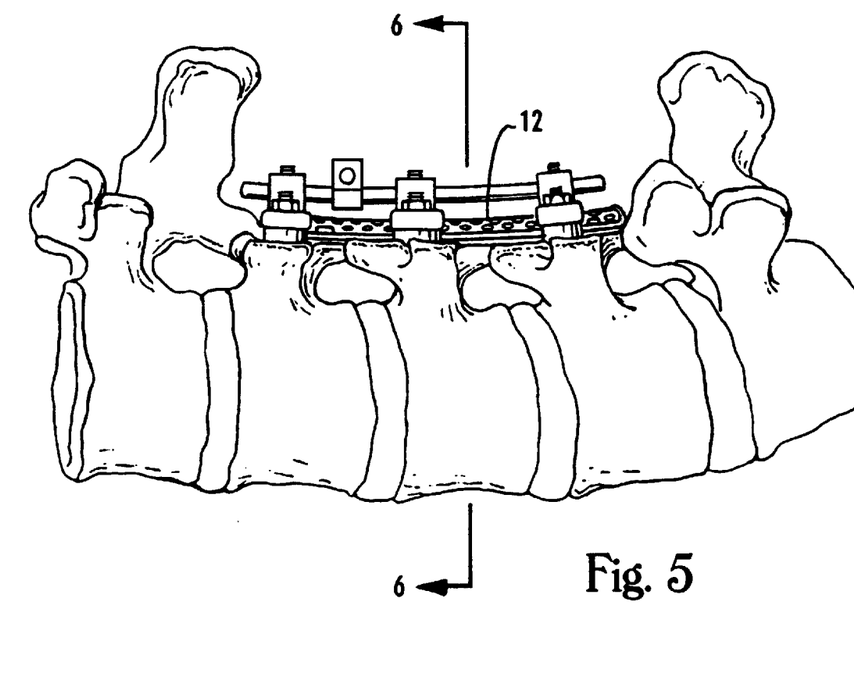
FIG. 5 is a partial side perspective view of the lumbar vertebrae showing another preferred embodiment of the present invention.

FIG. 4A provides an illustration of the bony dissection associated with a hemilaminectomy. Since the dissection for a hemilaminectomy is smaller than that of a laminectomy, it is contemplated that the surgeon, using a scalpel, or the like will be able to readily customize the shield 10 as sized for the laminectomy to overlie the exposed dura after a hemilaminectomy procedure. An example of a customized shield 10a contemplated for use in a hemilaminectomy is provided in FIG. 4B. The customized shield 10a is attached to the vertebrae 26 using the set of attachment pins 20.

Alternatively, it is contemplated that the shield 10 of FIG. 1 could be customized for a hemilaminectomy by removing one of the attachment arms 16. The remaining attachment arm 16 serves as an attachment means to anchor the shield 10 to a superior or an inferior spinous process.

It is further contemplated that the overall length of the shield 10 can be varied to accommodate laminectomies or hemilaminectomies involving more than one vertebrae. Thus, for example, in a laminectomy procedure involving the third, fourth and fifth lumbar vertebrae, the shield is preferably about 6.0 cm to about 12 cm in length and more preferably about 6.5 cm to about 9 cm in length. The width is preferably about 2.0 cm to 5.0 cm and more preferably about 2.0 cm to 3.5 cm.

As illustrated in FIG. 1, the main body 11 of the shield 10 preferably has an arch shape, and height h that prevents contact between the spinal dura and the surface of the shield 10. Preferably, the height h of the arch is between about 0.2 cm and 4.5 cm from the support planes 12, although within this range, it is contemplated that the shield 10 will be manufactured in at least two separate ranges of arch heights.

It is further contemplated that the arch height h can be varied to accommodate other medical devices known in the art. In a particularly preferred embodiment, the height h of the arch is between about 0.2 cm to 1.5 cm, or about one-half the height of an adjacent spinous process when positioned on the patient, and is used with medical devices such as a Dynamic Transverse Traction ("DTT") unit or other instrumentation systems employing a plurality of pedicle screws 34, (see FIG. 5) such as the Steffee-VSP system (AcroMed Corporation), Isola instrumentation (AcroMed Corporation, Cleveland, Ohio), or the like. The use of the shield 10 with such a device is illustrated in FIG. 5 in side view and in FIG. 6 in cross-section.

Figure 6:
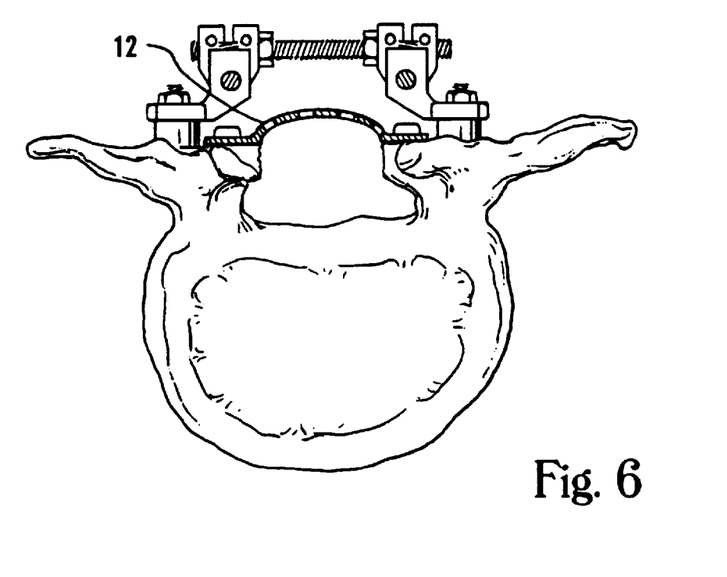
FIG. 6 is a sectional view taken substantially along the line 6—6 of FIG. 5, showing the positioning of the arched shield in accordance with a preferred embodiment of the present invention.

DTTs are particularly useful where lumbar segmental instability is a problem. The pedicle screws 34 and transverse rods 36 associated with these devices tend to restrict the placement of a spinal cord protective device over the spinal canal. The shield 10 that is suitable for a DTT device, or the like, preferably has a height h smaller than the dimension of the height between the DTT construct and the exposed dura. The reduced arch size permits the positioning of the spinal cord protection device beneath the pedical screws 34 and the transverse rods 36 without impingement. In such a case, the shield 10 is anchored to the vertebrae 26 through the fenestrations 14. Alternatively, the shield 10 may be anchored at its periphery to the adjacent facets or spinous processes 32 above or below the decompression, using anchoring pins together with the anchoring means associated with the fenestrations 14.

It is contemplated that the shield 10 of this invention may be prepared from any number of materials known in the art. It is contemplated that the device could be prepared from surgical steel including a woven metal fiber or other similar material. In a preferred embodiment of this invention, the device is prepared from a thermoplastic polymer such as polypropylene, polyethylene, polymethacrylate or the like. Other materials contemplated for use in this invention include, but are not limited to, tungsten, titanium, polytetrafluoroethylene, silicone, bioerodable polylactic acid, hydroxylapatite, regenerated collagen or the like. Those with skill in the art of medical devices will be readily able to select and formulate a composition having the preferred characteristics herein described.

Preferably, the material is biocompatible and is capable of being cut with a standard surgical tool, such as a scalpel, knife or scissors to permit customization of the device in the operating room to the shape and size of the bone defect for each individual patient. Methods for manufacturing the device of this invention will depend on the choice of material. Those with skill in the art of manufacturing implantable medical devices will be readily able to use the description of the invention provided herein to produce the contemplated spinal cord protection device. Thus, the device of this invention can be tooled, molded, heat pressed or the like. It is further contemplated that, depending on the selection of material for manufacturing the device of this invention, the device may have some pliability, such that the surgeon can customize the device to fit the desired bony dissection and, in addition, the shield 10 can be further bent or molded by the surgeon to accommodate the particular topography of the patient's spine.

The device of this invention may be prepared from a solid sheet of material, or the device can advantageously be prepared as a laminate. For those embodiments where the device is a composite of laminated sheets, it is possible to include or incorporate a radiopaque material as a laminated sheet into the device. Similarly the shield material can be impregnated with a radiopaque substance or incorporate a radiopaque material into the edges of the device. Suitable radiopaque materials include metals or halogenated compounds such as iodinated or brominated compounds. Other compounds include barium containing substances, renografin or commercially available, Isovue® (Squibb Diagnostics, Princeton, N.J.). Thus, the polymers contemplated for use in preparing the shield of this invention are preferably halogenated or are prepared in combination with halogenated polymers.

The presence of a radiopaque material in the shield 10 permits visualization of the shield 10 by X-ray radiation or the like. In situations where the patient's back pain persists or where revision surgery is contemplated, the surgeon is able to determine the position of the shield device of this invention prior to or during the revision surgery. The radiopaque substance also allows the surgeon to verify the location of the bone dissection as determined from the position of the shield.

It is further contemplated that the shield 10 of the invention can advantageously be impregnated with, or otherwise positioned in place in association with, a drug suitable for inhibiting the formation of adhesions. Therefore, in another preferred embodiment, the shield contains an absorptive, saturatable or impregnatable material suitable for acting as a carrier for an adhesion-inhibiting substance. Suitable adhesion-inhibiting drugs contemplated for use in association with the shield 10 of this invention include, but are not limited to, heparin salts and analogs of heparin salts, such as Pentosan Polysulfate ("PPS", available, for example, from Sigma Chemical Company, St. Louis, Mo.) or the like, or growth factor inhibitors or other compounds recognized in the art to inhibit adhesion formation. Further, compounds such as gelatin foams such as Gelfoam® sponge or Avitene® (MedChem, Inc. Woodburn, Mass.) can additionally be used together with the shield 10 of this invention to further reduce the incidence of adhesions following surgery.

One of the important advantages of this invention, over gelatin foams and other materials used in the art, is that the device facilitates revision surgery. Revision surgery is complicated by the formation of adhesions to the spinal dura. Dissections of adhesions and scar formation increase the time the patient must be under anaesthesia. Moreover, dissection of the scar tissue can result in inadvertent pierces or tears in the dura and the release of spinal fluid into the surgical area that can further complicate surgery. The spinal cord protection device prevents adhesions with the dura. During revision surgery, the surgeon can cut through the muscle and facia to the device quickly without the potential of piercing or tearing the spinal dura.

To further facilitate revision surgery, it is contemplated that in another preferred embodiment of this invention, the shield 10 is colored. It is contemplated that the selected dye will contrast in color with bone, blood or internal tissues, and thus further facilitate revision surgery since the surgeon can rapidly identify the shield 10 during the dissection process. Thus, contrasting colors contemplated for use with this device include shades of blue, green, black, purple, yellow, orange or the like.

While this invention is described in association with lumbar vertebrae, it is contemplated that the shield 10 of this invention is suitable for the cervical and thoracic regions of the spine as well. Further, as disclosed supra, the shield 10 is contemplated for use in any location in the body associated with a bony dissection.

The shield 10 of the present invention is contemplated to be commercially available in a number of different sizes, shapes and include various attachment means. The shields preferably are packaged in separate sterile packaging and can be arranged on a tray that includes single and multiple protector devices in different sizes and embodiments.

An exemplary surgical procedure employing the shield 10 of this invention is provided in Example 1, below. This procedure is only exemplary. Surgeons skilled in the art of orthopaedics and neurosurgery will be readily able to adapt their surgical techniques and surgical procedures to include the use of this shield and in particular, those surgeons skilled in spinal surgery will readily appreciate the variations discussed herein that do not detract from the scope of this invention.

In another aspect of this invention, the device is positioned between a target organ or tissue and the dermis to protect that organ or tissue from damage during the accessing stage of a subsequent surgical procedure. The protector device is positioned over the organ or tissue and is preferably anchored to bone, cartilage or muscle. When revision surgery is necessary, the surgeon can rapidly access the protector device without the risk of nicking or damaging the underlying organ or tissue. The protector device can then be removed to expose the target tissue or organ.

It is contemplated that the device will also facilitate revision surgery by minimizing post-operative adhesion formation. Post-operative adhesion formation complicates a wide variety of revision surgeries. As discussed above, these adhesions make dissection tedious because the adjacent bone or tissue is now adhered to the target organ. This increases the likelihood that the organ will be inadvertently damaged during the surgical procedure. The presence of adhesions dramatically increases the time that a person is under anesthesia. The present invention overcomes these problems by creating a barrier that minimizes adhesion formation between adjacent tissue plans and protects the surgical area from damage during the accessing phase of a subsequent revision surgery.

One application of the adhesion inhibitor of the present invention is following open heart surgery. Adhesions form between the pericardium and the posterior surface of the sternum following a variety of open-heart cardiac procedures that disrupt the pericardium and the linings of the greater vessels of the heart. In particular, children who have congenital cardiac defects often require multiple surgical procedures over their lifetimes. In addition, a significant percentage of individuals who receive cardiac bypass surgery will require a second cardiac procedure months or years after their original bypass surgery. A common problem associated with these surgeries is that adhesions form between the posterior portion of the sternum and the anterior portion of the pericardium of the heart following surgery. These adhesions complicate subsequent surgeries because the heart is affixed to the sternum during the second sternotomy procedure. The surgeon must tediously dissect both pericardial adhesions and adhesions forming between the greater vessels of the heart and the sternum before performing the sternotomy.

Adhesions are particularly a problem for those revision cardiac surgeries that employ portions of the internal mammary artery for bypass tissue. Since the internal mammary artery has a higher degree of patency than the saphenous vein, or other veins of the lower extremity typically used for the bypass procedure, the dissection process required to release the heart from the sternum in a revision surgery is relatively complex. However, for a number of other reasons, the internal mammary artery is the vessel of choice for current bypass surgeries. These dissections are an obligate step of the revision surgery and increase the amount of time required to perform the second surgery and complicate the surgical procedure by increasing the risk that the heart will be inadvertently lacerated, nicked or otherwise damaged. The lacerations or nicks to the heart and greater vessels may result in serious complications or catastrophic results.

Figures 7, 8A, 8B, 9:
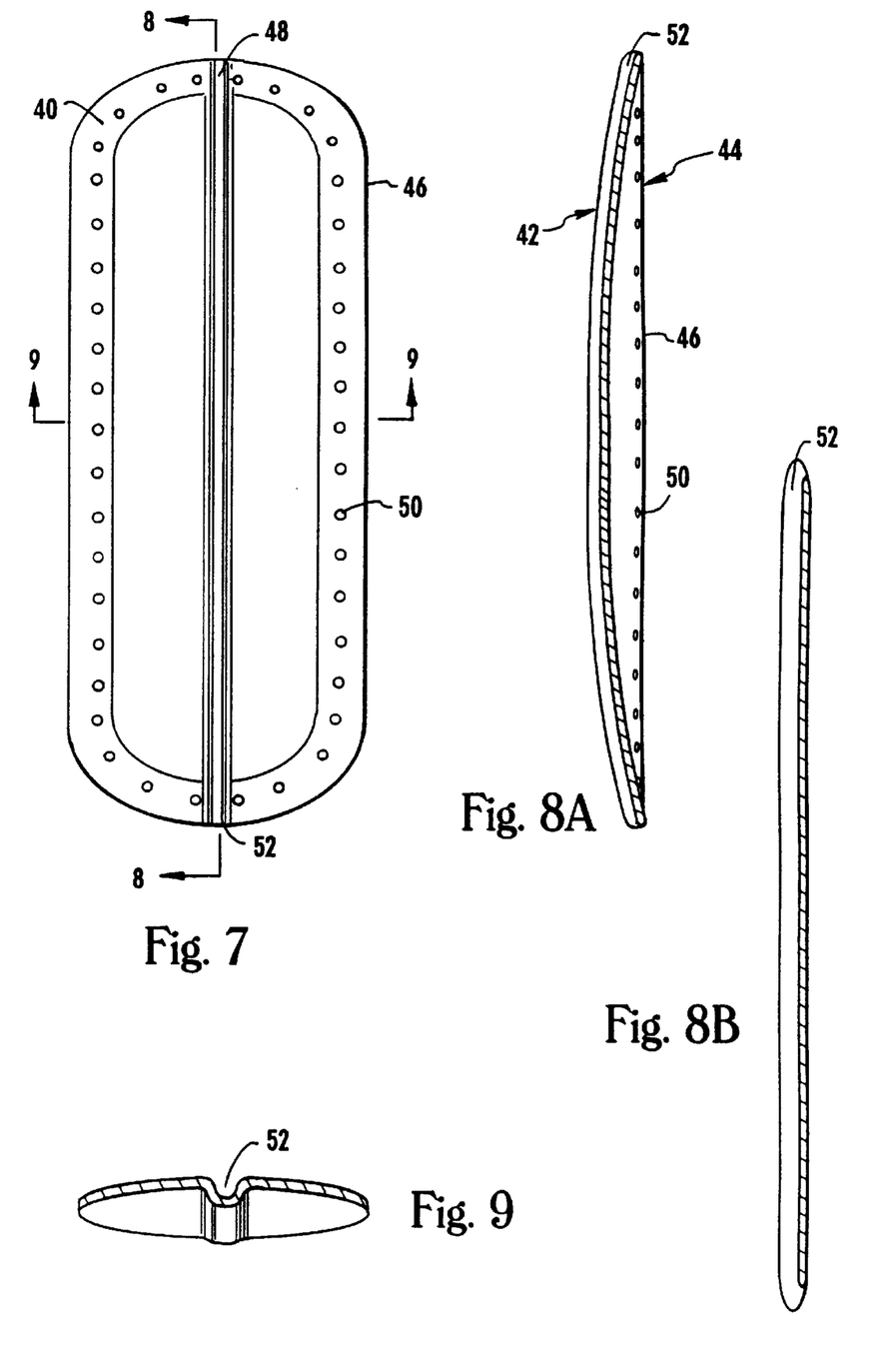
FIG. 7 is a top plan view showing an exemplary cardiac protector device of this invention.
FIG. 8A is a longitudinal cross-section of the device taken substantially along the line 8—8 of FIG. 7 illustrating the curved shield embodiment.
FIG. 8B is a longitudinal cross-section of the device illustrating the flat shield embodiment.
FIG. 9 is a transverse cross-section of the device taken substantially along the line 9—9 of FIG. 7 illustrating the longitudinal guide.
Figure 10:
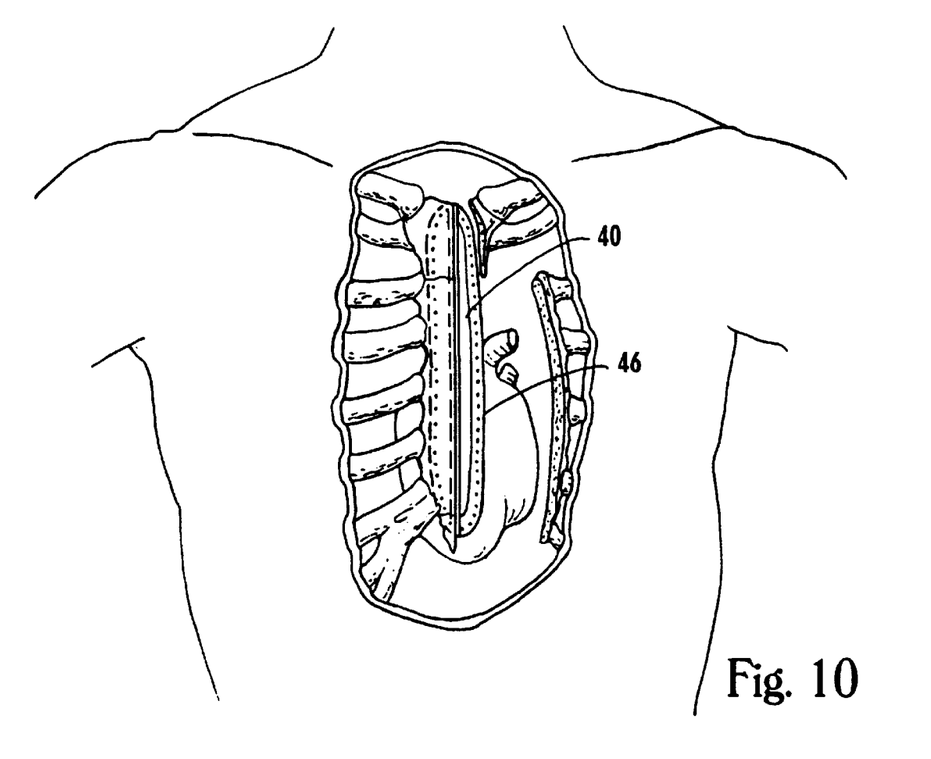
FIG. 10 is a perspective view illustrating the position of the device relative to the heart and the anterior thoracic skeleton.

An example of the type of adhesion-minimizing protector device contemplated in this invention is illustrated in FIG. 7. This device is adapted to facilitate repeat open heart surgeries. The body of the device 40, also known as a shield, is preferably substantially oblong in shape. It is also contemplated that the device can be substantially circular or substantially rectangular in shape; however, as illustrated in FIG. 7, the edges of the device are preferably rounded and smoothed to reduce abrasion and bruising of the surrounding tissue after implantation. Thus, the use of the term "substantially oblong" is used herein to mean that the overall conformation of the anterior surface of the device is generally similar to a geometric oblong.

Figure 11:
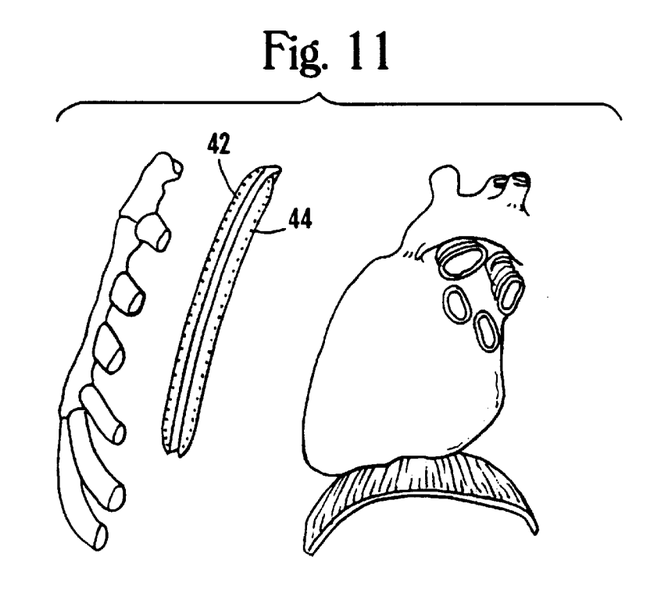
FIG. 11 is an exploded perspective view further illustrating the position of the device relative to the heart and rib cage.

In one embodiment, the device is generally flat (FIG. 8B) such that both its anterior surface 42 (see FIG. 11), that is adjacent to the sternum, and the posterior surface 44, that portion of the device that is adjacent the heart, form a substantially flat plane. In another embodiment, illustrated in FIG. 8A, the body of the device is curved along at least one axis, such that the body forms a portion of the face of a cylinder, with the posterior surface 44 of the device forming a concavity. The concavity is preferably slight such that the longitudinal edges 46 of the device are minimally raised relative to a central longitudinal line 48 that spatially divides the device lengthwise. The arch height h of the device is defined as the distance between the plane which connects the opposing longitudinal edges 46 of the device and the parallel plane tangent to the device at the central longitudinal line 48. It is anticipated that the degree of curvature or concavity will be no more than that required for the device to rest comfortably between the heart and the sternum.

Anchoring means are preferably provided along the edges of the device 40. In one embodiment of this device, the anchoring means comprise fenestrations or anchoring ports 50 (see FIG. 7). Preferably, the anchoring ports are large enough to accommodate suture or wire. It is contemplated that the cardiac protector device will be anchored to the central anterior portion of the thoracic skeleton. Thus, the device can be anchored to bone, cartilage, muscle or supportive elements associated with the central anterior portion of the thoracic skeleton, including the sternum. The anchoring means stabilize the device and prevent it from moving with the normal pulsation of the heart. Further, the anchoring means prevent the device from moving during normal thoracic movement. It is contemplated that enough anchoring ports are provided to permit the device to be anchored in place irrespective of the position of the device relative to the sternum. While FIG. 7 provides one example of a device having fenestrations circumscribing the periphery of the apparatus; it is further contemplated that the fenestrations can be limited to the cranial and caudal aspects of the device. A method for attaching the device in place following open heart surgery is provided in Example 2.

In one embodiment of the cardiac protector device, a longitudinal guide 52 extends along the length of the anterior surface of the device following the central longitudinal line 48. This longitudinal guide is positioned beneath the sternum along the sternotomy line. In the embodiment illustrated in FIG. 7 and by cross-section in FIG. 9, the guide forms a longitudinal cutting guide extending along the length of the device. The longitudinal guide advantageously facilitates revision surgery by providing a recess to further distance the device from the sternum midline. This recess facilitates the positioning of the oscillating saw, or other equivalent surgical tool, along the sternum. Thus, the longitudinal guide serves as a groove for the surgeon to follow as he or she cuts through the sternum. An exemplary surgery using a cardiac protector device having a longitudinal guide is provided in Example 3.

The dimensions of the device may vary in length such that the device extends the full length of the sternum, or alternatively the device may be just a few inches in length. Therefore, it is contemplated that the device will range in length l from about 3.0 to 10 inches and more preferably from about 4.0 to 8.5 inches. The width w of the device is preferably from about 0.5 to 4.0 inches and more preferably from about 1.0 to 3.0 inches. The thickness of the device may vary from 0.125 to 0.5 inches and preferably from between 0.125 to 0.375 inches. In those embodiments where the body of the device is curved, the arch height h of the device is preferable no greater than 0.5 inches.

The dimensions can be selected and readily optimized by one of skill in the art in view of the disclosure herein, depending upon the particular surgical site and patient size. It is further contemplated that the dimensions of the apparatus may be scaled down even further to accommodate infant and pediatric applications for cardiac procedures were multiple surgeries are likely.

The body of the cardiac protection device 40 is preferably prepared from a biocompatible material that is capable of being cut with a standard surgical tool, such as a scalpel, knife, or scissors (such as a Mayo or Metsenbaum type scissor) to permit customization of the device in the operating room. In a particularly preferred embodiment, the device is sufficiently malleable so that the device can be molded and contoured by the surgeon at the time of the surgery to accommodate the coronary artery bypass graft employing the internal mammary artery as its primary vessel. Alternatively, the device can be preformed in its final configuration from any of a variety of materials such as stainless steel, injection moldable polymers, and the like as will be apparent to one of skill in the art.

Preferably, the device is prepared from a thermoplastic polymer such as polypropylene, polyethylene, poly-methacrylate or the like. It is further contemplated that the device, once formed, is somewhat flexible. Therefore, other materials also contemplated for use in this invention include, but are not limited to, silicone, bioerodable polylactic acid, poly-HEMA, or the like. Those with skill in the art will be able to select a suitable biocompatible material.

It is also contemplated that even more flexible materials will be selected for other protection device applications, including between adjacent soft tissue planes. These devices are then suitable for minimizing adhesion formation following abdominal surgery, urogenital surgery, tendon surgery, hip surgery or the like.

In yet another embodiment of this device, the device is provided without anchoring ports. In this embodiment, the device is prepared from a material that can be punctured by a sharp object to permit the surgeon to form his or her own anchoring ports during the surgical procedure.

It is further contemplated that the device can be tooled, molded, heat pressed or the like. The methods of manufacturing the device will depend on the choice of material. Those with skill in the art of manufacturing implantable medical devices will be readily able to use this description of the contemplated invention together with the FIGURES to produce the protector device of this invention.

Like the spinal cord protection device, it is contemplated that the cardiac protection device can be prepared from a solid sheet of material, or the device can be prepared as a laminate. A radiopaque material is preferably incorporated into the device either as a laminate or the radiopaque substance can be impregnated either throughout the device or along the periphery. Suitable radiopaque materials are disclosed in the discussion relating to the spinal cord protection device (supra). FIG. 7 illustrates a preferred embodiment having a radiopaque material such as barium or the like incorporated into the device as a peripheral ring 54.

It is further contemplated that the body of the device, like the spinal cord protection device described above, can be impregnated with, coated with, or otherwise positioned in place in association with a drug or other substance suitable for inhibiting the formation of adhesions. Suitable adhesion-inhibiting drugs contemplated for use in association with the cardiac protection device include, but are not limited to, heparin salts and analogs of heparin salts, such as Pentosan Polysulfate, hyaluronic acid, dextran, growth factor inhibitors, or other compounds recognized in the art to inhibit adhesion formation such as gelatin foams, or the like.

Like the spinal cord protection device, it is contemplated that the body of the cardiac protection device is colored to contrast with the color of bone, fascia, blood and heart tissue. Thus, contrasting colors contemplated for use with this device include shades of blue, green, black, purple, yellow, pink, or the like.

Particular embodiments of the invention will be discussed in detail and reference has been made to possible variations within the scope of the invention. There are a variety of alternative adaptations and surgical procedures available to those of skill in the art which would similarly permit one to successfully produce and use the intended embodiments of this invention.

EXAMPLE 1

Laminectomy and Decompression Surgery Involving the Surgical Positioning of the Spinal Cord Protection Device The surgical tools disclosed herein are standard surgical equipment well known to those skilled in the art of orthopaedic and neurosurgery. The patient is positioned on an Andrew's frame or operating table and prepped and draped in the fashion standard for back surgery. The incision is made over the spinous process of the area to be decompressed. The incision is carried down through the dorsal lumbar fascia and the fascia is then incised down to the spinal lamina junction. Dissection is continued out to the tips of the transverse processes and is accomplished using the electrocautery and Cobb dissection tool. Self retaining retractors are then placed into the wound to allow clear visualization of the structures which have been denuded of their soft tissue. Further meticulous soft tissue dissection is performed with the removal of the supraspinous ligament and the interspinous ligament for the vertebral levels to be addressed in the surgery process. Intraoperative lateral x-ray confirms the position at the appropriate level. A Lexzell rongeur is then used to remove the bone of the spinous process 32 and that portion of the lamina 40 (see FIG. 3A). A Kerrison rongeur is used to remove bone from the lamina as well as ligamentum flavum and epidural fat.

The dissection is carried out to the facet joints. If nerve root entrapment, either by disk or soft tissue is noted lateral to the facet, then a partial medial facetectomy is performed. The origin of the nerve roots are then identified and traced into their corresponding neural foramen.

A neural foraminal probe is placed into the neural foramen at each level and if it is met with any impedance, a partial foraminotomy is performed at each level to facilitate the passage of the probe. Once this is completed, hemostasis is achieved using the Malis bipolar coagulator or electrocautery device.

Dissection into the neural foramen many times can result in increased instability by weakening the facet region. In order to minimize this, a 4 mm burr is used to do the dissection in the opening of the neural foramen to minimize the destruction with the Kerrison rongeur. The operative area is then irrigated and suction dried, and once again hemostasis is achieved using electrocautery and a Malis bipolar coagulator.

Following the corrective surgery to the spinal column, the spinal cord protection shield 10 is positioned over the laminectomy defect (see FIG. 3B). Customization of the shield 10 is performed with a scalpel and scissors thereby molding the shield 10 to conform with the individual contours of the spinal column. The angle of the attachment arms relative to the protector device is adjusted by manually deforming the attachment arms to facilitate their attachment to an adjacent spinous process. The arms are sutured in place onto the spinous process and the fenestrations on the shield body are additionally used to suture the device in place (see FIG. 3B).

The wound is closed using standard operating procedures, a drain is preferably placed into the wound and, as one example of wound closure, the wound is closed in layers using a #1 Vicryl (Ethicon, Piscataway, N.J.) suture for the dorsal lumbar fascia, a 2-0 Vicryl for the deep subcutaneous tissue, and a 3-0 subcuticular stitch.

EXAMPLE 2

Method for Inserting the Cardiac Protection Device

Those with skill in the art of heart surgeries will recognize that there are a variety of surgical methods recognized in the art for performing cardiac surgeries and that each surgeon is familiar with his or her own preferred surgical strategy. This Example is intended only to teach one with skill in the art how the device of this invention can be incorporated into one physician's particular surgical procedure.

The patient is positioned in a supine manner on the operating table and the chest, upper abdomen and lower extremities are prepped for surgery. After the patient has been prepped a sterile drape is applied to the chest, lower extremities, abdomen and the perineum. The chest and lower extremities are draped out separately and kept sterile through the entire procedure to facilitate vein harvesting in the lower extremities. One team of physicians opens the heart and a second team harvests the graft of the saphenous vein from the lower extremity. The vein is usually harvested in toto. The chest is opened using an oscillating saw along the midportion of the sternum. Once the sternum is divided, the anterior portion of the chest is opened to expose the anterior portions of the right and left chest cavities. The surgeon then performs the bypass procedure.

When the surgical procedure is complete, the cardiac protection device is attached to the posterior aspect of the sternum. Preferably the device incorporates an adhesion-inhibiting compound such as a heparin analog, or the like. The attachment is accomplished as the lateral aspects of the sternum are brought together. The device is attached to the sternum by running anchoring sutures or wires through the sternum to the device at its periphery. No more than one or two securing stitches positioned at the cranial and caudal aspects of the device are generally required to position the device in place. The sternum halves are wired together and the incision is closed using standard procedures for cardiac surgery wound closure.

EXAMPLE 3

Method for Accessing the Heart with a Cardiac Protection Device in Place

The following method is useful for accessing the thoracic cavity for a revision cardiac bypass surgery in a patient having a cardiac protection device in place. Once the sternum is exposed, a Stryker sternal saw (such as a straight Stryker sternal saw (298-97-100) or a half moon Stryker sagittal saw (2108-137) (Stryker Medical Supply) is positioned along the manubrium of the sternum with the blade positioned between the sternum and the cardiac protection device. The half moon Stryker sagittal saw is preferably used in revision coronary artery bypass surgery. The longitudinal guide in the device is used as a path to move the saw down the sternum. The sutures are clipped to separate the device from the sternum and the rib cage is separated to expose the thoracic cavity. The protector device is removed to expose the heart.

While particular embodiments of the invention have been described in detail, it will be apparent to those skilled in the art that these embodiments are exemplary rather than limiting, and the true scope of the invention is that defined in the following claims.

What is claimed is:

1. A surgical kit comprising:
   at least one shield adapted to cover a bony dissection in the spine of a vertebrate, said shield comprising attachment ports proximate to an edge of said shield and configured to accept attachment pins for attaching said shield to bone, said shield also comprising fenestrations, and said shield comprising an elongate concavity for maintaining said shield away from the spinal dura following installation, and
   a plurality of attachment pins for attaching said shield to bone.

2. The surgical kit of claim 1, wherein said shield is at least partially prepared from bioerodable material.

3. A surgical kit comprising:
   at least one shield adapted to cover a bony dissection in the spine of a vertebrate, said shield comprising attachment ports proximate to an edge of said shield and configured to accept attachment pins for attaching said shield to bone, said shield also comprising fenestrations, and wherein said shield is substantially pliable, and
   a plurality of attachment pins for attaching said shield to bone.

4. The surgical kit of claim 3, wherein said shield is at least partially prepared from bioerodable material.

5. A protection device comprising:
   a substantially pliable shield adapted to cover a bony dissection in the spine of a vertebrate, said shield having an elongate concavity extending axially along said shield, said a first support plane spaced laterally apart from the longitudinal axis of said shield in a first direction, a second support plane spaced laterally apart from the longitudinal axis of said shield in a second direction, said shield further comprising attachment arms for attaching said shield to bone configured such that said support planes can contact portions of said spine while contact between the spinal dura and the entire protection device is substantially avoided, wherein said shield is at least partially prepared from bioerodable material.

6. A method of performing spinal surgery comprising the steps of:
   performing a bony dissection on at least a portion of one vertebrae to expose the spinal dura; and
   positioning a bioerodable shield to cover said exposed spinal dura, wherein said shield covers at least a portion of one vertebrae having said bony dissection, wherein said shield is spaced apart from the spinal dura.

* * * * *